United States Patent
Balschat et al.

(10) Patent No.: US 8,315,654 B2
(45) Date of Patent: Nov. 20, 2012

(54) EXTRACORPOREAL BLOOD TREATMENT DEVICE AND METHOD FOR PREPARING BLOOD TREATMENT USING AN EXTRACORPOREAL BLOOD TREATMENT DEVICE

(75) Inventors: Klaus Balschat, Schwebheim (DE);
Pascal Kopperschmidt, Dittelbrunn (DE); Reiner Spickermann, Wasserlosen-Burghausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 681 days.

(21) Appl. No.: 12/438,775

(22) PCT Filed: Aug. 22, 2007

(86) PCT No.: PCT/EP2007/007369
§ 371 (c)(1),
(2), (4) Date: Nov. 9, 2009

(87) PCT Pub. No.: WO2008/025467
PCT Pub. Date: Mar. 6, 2008

(65) Prior Publication Data
US 2010/0323724 A1    Dec. 23, 2010

(30) Foreign Application Priority Data
Aug. 26, 2006 (DE) .......................... 10 2006 040 179

(51) Int. Cl.
*H04W 4/12* (2009.01)
(52) U.S. Cl. ...................................... 455/466; 604/5.01
(58) Field of Classification Search .................. 455/466, 455/41.2; 604/5.01; 210/645
See application file for complete search history.

(56) References Cited

U.S. PATENT DOCUMENTS

| | | | |
|---|---|---|---|
| 5,276,611 A | 1/1994 | Ghiraldi | |
| 6,730,026 B2 | 5/2004 | Christ et al. | |
| 7,044,927 B2 | 5/2006 | Mueller et al. | |
| 2004/0203961 A1* | 10/2004 | Rustici et al. | 455/466 |
| 2006/0184084 A1* | 8/2006 | Ware et al. | 604/5.01 |

FOREIGN PATENT DOCUMENTS

| | | |
|---|---|---|
| DE | 102006040179 B3 | 8/2006 |
| EP | 0428676 B1 | 5/1991 |
| EP | 1101437 A1 | 5/2001 |
| EP | 1226781 A2 | 7/2002 |
| JP | 11033110 A | 9/1999 |
| WO | 90/14850 A1 | 12/1990 |
| WO | 01/45767 A2 | 6/2001 |

OTHER PUBLICATIONS

International Search Report, PCT/EP2007/007369, mailed Feb. 26, 2008.

* cited by examiner

*Primary Examiner* — Phuoc Doan
(74) *Attorney, Agent, or Firm* — Kenyon & Kenyon LLP

(57) ABSTRACT

The present invention relates to an extracorporeal blood treatment device comprising a treatment unit and a device for controlling the treatment unit for preparing and carrying out the blood treatment. The blood treatment device also comprises an internal communication unit for communicating with an external communication unit. In order to the prepare the device blood treatment, the patient sends an initiation code by means of an external communication unit to the internal communication device. Routines required for preparing the blood treatment are then started. One main advantage is that the patient, for example during home dialysis, does not need to be present when the device is preparing for dialysis and the dialysis preparation can be started when the patient thinks of returning home in time for the beginning of the preparation phase.

12 Claims, 1 Drawing Sheet

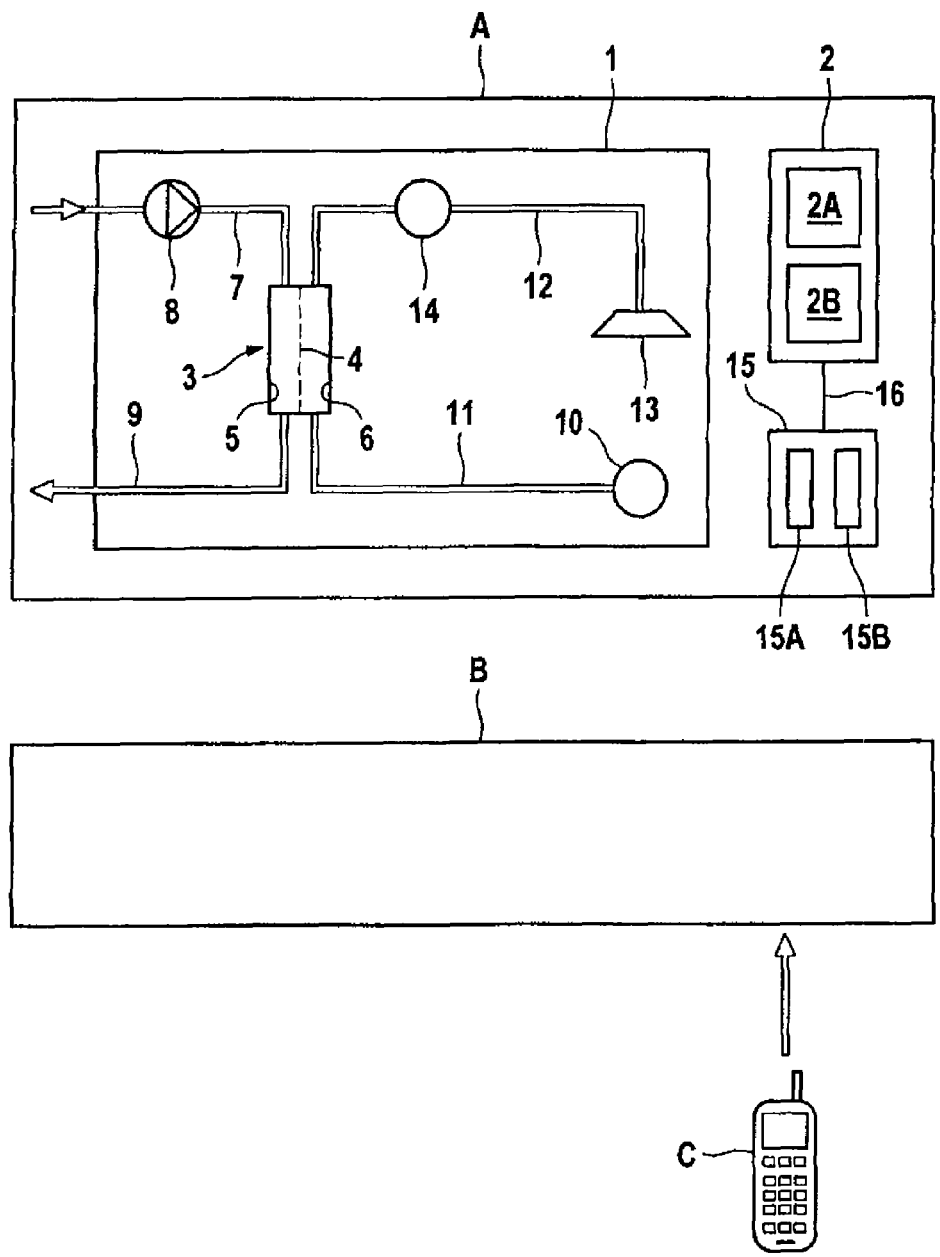

US 8,315,654 B2

EXTRACORPOREAL BLOOD TREATMENT DEVICE AND METHOD FOR PREPARING BLOOD TREATMENT USING AN EXTRACORPOREAL BLOOD TREATMENT DEVICE

CROSS REFERENCE TO RELATED APPLICATIONS

This is a 371 national phase application of PCT/EP2007/007369 filed Aug. 22, 2007, claiming priority to German Patent Application No. 10 2006 040 179.4 filed Aug. 26, 2006.

FIELD OF INVENTION

The present invention relates to an extracorporeal blood treatment apparatus which has an internal communication unit for communication with an external communication unit. Moreover, the present invention relates to an arrangement consisting of an extracorporeal blood treatment apparatus, which has an internal communication unit, a communication network and an external communication unit for communication with the internal communication unit via the communication network. Furthermore, the present invention relates to a method for the preparation of a blood treatment with an extracorporeal blood treatment apparatus which has an internal communication unit for communication with an external communication unit.

BACKGROUND OF THE INVENTION

Hemodialysis, hemofiltration and hemodiafiltration are known as methods for extracorporeal blood treatment. Dependence on extracorporeal blood treatment apparatuses, for example dialysis machines, restricts the patient's quality of life.

Hemodialysis can be carried out in dialysis centers or also at home (home dialysis). Whereas the dialysis machine is operated by the nursing staff in dialysis centers, the patient has to operate the dialysis machine independently in the case of home dialysis. Home dialysis has the advantage, however, that the dialysis can be carried out in the patient's familiar surroundings, as a result of which the patient's quality of life is improved.

There is known from U.S. Pat. No. 7,044,927 an extracorporeal blood treatment system, which has an extracorporeal blood treatment apparatus which provides a communication via a public communication network, so that a plurality of dialysis machines can, for example, be monitored from a control centre. Moreover, there is the possibility of setting up a service center, in which a chosen service technician for maintenance work can monitor the components of the machine and undertake adjustments to the machine. Furthermore, it is possible to transmit data, for example patient-related information, in order to be informed about the patient's condition at another location. The known blood treatment system makes use of a Web server and Web browser. Access to the blood treatment apparatus requires suitable authorization.

It is known from US 2004/0203961 for home dialysis patients to send a short message (SMS) to nursing staff by means of a mobile telephone as part of patient monitoring. The sending of an SMS, however, is only intended to be used for the purpose of informing nursing staff. No data are transmitted to the dialysis machine itself.

EP 1 101 437 A1 and EP 1 226 781 A2 describe a medical system for monitoring a patient's parameters in the home environment, wherein the doctor is informed by e-mail in urgent cases or messages are sent by SMS for information purposes.

Outside the sphere of medical technology, it is known for example to transmit data between a provider and the machine via a public communication network for the purpose of time recording for service and accounting purposes.

The operation of the dialysis machine requires certain time-intensive procedures for the preparation of the treatment. At the start of the treatment, it is necessary for example to ensure the supply of various fluids to the dialysis machine. This includes, in particular, the rinsing and filling of individual components with rinsing fluid and dialysing fluid. Moreover, various test routines are carried out in order to guarantee a reliable operation of the dialysis machine during the blood treatment. An attempt is generally made with dialysis machines to automate as completely as possible the procedures required for the preparation of the dialysis treatment.

During the preparation of the dialysis machine, it is not absolutely essential for the patient to be present. Since the preparation of the machine is time-intensive, the patient's presence means a further loss of quality of life. An attempt is therefore made to carry out the preparation of dialysis automatically in the patient's absence. As a result, however, the problem arises that the patient has to plan his daily routine precisely, in order to be present promptly after completion of the preparatory procedures. This is because a delayed start of the treatment would lead to a considerable waste of operating resources.

The quality of life of home dialysis patients in particular could be further improved if the dialysis patient did not have to stay at home during the preparation of the dialysis machine.

US 2006/0184084 A1 describes an arrangement which comprises a dialysis apparatus and a plurality of external input/output devices. The input/output devices communicate with the dialysis apparatus via wireless links. The network is intended to serve amongst other things to simplify the initialization of a dialysis treatment.

The combining of items of extracorporeal blood treatment equipment and input and output devices into a network is also known from JP 11033110 A.

EP 0 428 676 B1 describes a dialysis apparatus which has a device for processing and storing signals associated with individual dialysis parameters. The known dialysis apparatus has a switching time clock with which it is possible to set the sequence over time in which the individual values are selected by the device for processing and storage. For example, a point in time at which the treatment will begin can be laid down.

SUMMARY OF THE INVENTION

One object of the present invention, therefore, is to provide an extracorporeal blood treatment apparatus which allows the patient to have the maximum possible freedom in planning the daily routine. A further object of the present invention consists in specifying a blood treatment system and a method for the preparation of a blood treatment with an extracorporeal blood treatment apparatus, which allows the patient the greatest possible freedom in planning his daily routine.

Like every conventional blood treatment apparatus, the extracorporeal blood treatment apparatus according to the invention has a treatment unit for the performance of the extracorporeal blood treatment. Apart from the actual treatment unit, the blood treatment apparatus according to the invention comprises a device for controlling the treatment unit for the performance of the extracorporeal blood treatment and a device for controlling the treatment unit for the preparation of the extracorporeal blood treatment. With the latter device, automatable processes are carried out which are required for the preparation of the blood treatment. These include for example rinsing, filling and test routines.

Moreover, the blood treatment apparatus according to the invention has an internal communication unit for communication with an external communication unit. The internal communication unit cooperates with the device for controlling the treatment unit for the preparation of the extracorporeal blood treatment in such a way that the device for the preparation of the blood treatment is started after an initiation code is received from the external communication unit.

With the blood treatment apparatus according to the invention, the patient can determine the time at which the blood treatment apparatus is prepared for the treatment by sending an initiation code with the external communication unit. It is assumed that the routines for the preparation of the treatment require for example a period of 30 minutes. In this period, the patient does not need to be present, so that he is free to determine the daily routine. Not until the patient is able to foresee that he can be at home for the home dialysis within 30 minutes does the patient start the preparation of the extracorporeal blood treatment, in that he sends an initiation code so that the treatment unit for the preparation of the blood treatment is started up.

The internal and external communication unit can be known communication units, which permit transmission of the initiation code via a line or a radio link.

In a preferred embodiment of the invention, the internal communication unit is designed as a mobile telephone unit and the external communication unit as a mobile telephone, wherein the initiation code is a short message in SMS format. By sending a particular SMS, the patient can thus start the preparatory routines at any time.

In principle, it is possible to start all the routines for the preparation of the blood treatment with an SMS. It is however also possible solely to start individual preparatory routines. For example, a different SMS can be provided in order to distinguish between different initiation routines.

A further preferred embodiment makes provision such that the initiation code contains a code for identification of a particular patient. The internal communication unit of the blood treatment apparatus has a device for storing a code for identification of a particular patient and a comparison unit for comparing the code contained in the initiation code in order to identify the patient with the stored identification code. If the stored code agrees with the code which is contained in the initiation code, the patient is considered to be identified. A misuse can thus be eliminated.

In the case where the internal communication unit is designed as a mobile telephone unit and the external communication unit as a mobile telephone, there is in principle no need for the identification of a particular patient, inasmuch as the mobile telephone unit is generally already identified as such by the telephone number when a call is made with a mobile telephone. The identification code may however also be an additional alphanumeric character string known only to the patient, said sequence being part of the SMS.

If the external mobile telephone is a conventional mobile telephone, the internal mobile telephone unit can be a modular unit which only permits the reception, but not the transmission of short messages (SMS). The only decisive factor is that both components are based on the known mobile telephone techniques which operate according to a known standard, for example GSM or UTSM, so that the existing communication networks can be used. The extracorporeal blood treatment apparatus according to the invention can thus be produced with a relatively small technical outlay.

Instead of a short message, a voice message, i.e. a word or a sequence of words (a sentence, for example) spoken by the patient, can also be used as an initiation code. To advantage, this can also easily be achieved with the known mobile telephone technology. If the initiation code is a voice message, a further authorization with known devices for speech recognition can take place in addition to the authorization by the use of the mobile telephone.

BRIEF DESCRIPTION OF THE DRAWINGS

An example of embodiment of the invention is explained below in greater detail by reference to FIG. 1, which shows in a very simplified representation an arrangement consisting of an extracorporeal blood treatment apparatus, a communication network and an external communication unit.

FIG. 1 shows only the main components of the extracorporeal blood treatment apparatus, since extracorporeal blood treatment apparatuses for hemodialysis, hemofiltration and hemodiafiltration as such are known to the person skilled in the art.

DETAILED DESCRIPTION OF THE DRAWINGS

Extracorporeal blood treatment apparatus A, for example a hemodialysis machine, has a treatment unit 1 and a device for controlling treatment unit 2. Treatment unit 1 is understood to mean all the components of the dialysis machine that are used to perform the actual dialysis, whilst control device 2 comprises all the components with which the components required for the performance of the dialysis are controlled.

The main components of the treatment unit will first be described in brief. Treatment unit 1 comprises a dialyser 3, which is divided by a semipermeable membrane 4 into a blood chamber 5 and a dialysing fluid chamber 6. An arterial blood line 7, into which a blood pump 8 is incorporated, leads from a patient to an inlet of blood chamber 5, whilst the venous blood line 9 leads from the outlet of the blood chamber 5 to the patient.

Fresh dialysing fluid is prepared in a dialysing fluid source 10. A dialysing fluid supply line 11 leads from dialysing fluid source 10 to an inlet of dialysing fluid chamber 6 of dialyser 2, whilst dialysing fluid discharge line 12 leads from the outlet of the dialysing fluid chamber 6 to a drain 13. A dialysing fluid pump 14 is incorporated into dialysing fluid discharge line 12.

Control device 2 can be a computer with suitable hardware components on which a control program runs. The control device assumes both the control of the treatment unit 1 for the performance of the dialysis as well as the control of the treatment unit 1 for the preparation of the dialysis. Control device 2A for controlling the performance of the dialysis and control device 2B for controlling the preparation of the dialysis are represented diagrammatically.

The dialysis machine also has an internal communication unit 15 for communication with an external communication unit. Internal communication unit 15 exchanges data with control device 2 via a data line 16.

For the preparation of the dialysis, control unit 2B controls various components of blood treatment unit 1 in order to take the measurements required for dialysis prior to connection of the patient to blood lines 7, 9. These measurements depend on the degree of automation of the dialysis machine which is described merely in abstract terms. The dialysis machine should preferably perform all the preparatory procedures automatically when control device 2B is started.

After the preparation of treatment unit 1 for the dialysis and the connection of the patient to blood lines 7, 9, control unit 2A is started for performance of the dialysis.

Apart from blood treatment apparatus A, the blood treatment system comprises a communication network B and an external communication unit C which is available to the patient. In principle, a number of communication units can be available to the patient.

External communication unit C and communication network B are preferably a conventional mobile telephone (cellular telephone) and a conventional mobile radiotelephone network. The patient can communicate using mobile telephone C via mobile radiotelephone network B with internal communication unit 15 of blood treatment apparatus A. In the case where external communication unit C is a mobile telephone, internal communication unit 15 comprises a conventional module which is used in the known mobile telephones.

The blood treatment system according to the present invention works as follows. The patient sends a short message (SMS) with mobile telephone C via communication network B to internal communication unit 15 of blood treatment apparatus A in order to prepare the blood treatment apparatus for the blood treatment. Internal communication unit 15 then starts control device 2A for the preparation of the dialysis, so that for example the dialysis machine is rinsed with rinsing fluid and filled with dialysing fluid and various test routines are performed.

The treatment system according to the invention is of advantage especially in home dialysis, where no staff are available to set up the dialysis machine. The patient does not need to be present during the preparation of the dialysis treatment. Since the patient knows the duration of the dialysis preparation, the patient sends the short message (SMS) when he knows that he will be at home after the lapse of this period.

Internal communication unit 15 starts the preparation of the dialysis only when a particular initiation code is received via a short message (SMS). This can be established in advance. Various short messages can also be established in order to start different preparatory routines.

An alternative embodiment of the invention makes provision to start the preparation of the dialysis not by means of a short message (SMS), but a voice message, and so a conventional mobile telephone can again preferably be used as an external communication unit C also in the case of the alternative embodiment. Instead of a short message (SMS), a voice message is now received and evaluated.

In order to ensure that the preparation of the dialysis machine can be started only by a particular patient by means of a mobile telephone, the initiation code contains a code for the identification of the patient. Internal communication unit 15 comprises a device 15A for storing a code for identification of a particular patient and a comparison unit 15B for comparing the code contained in the initiation code in order to identify the patient, for example a particular alphanumeric character string as part of the SMS.

When internal communication unit 15 receives the identification code sent by the patient by means of external communication unit C, comparison unit 15B compares the received code with the stored code in order to check whether the received identification code corresponds to the stored identification code. Only if this is the case does the internal communication unit start control device 2B for the preparation of the blood treatment.

The invention claimed is:

1. An extracorporeal blood treatment apparatus comprising:
    a treatment unit for performing the extracorporeal treatment;
    a first controller for controlling preparation of the treatment unit;
    an internal communication unit configured to communicate with an external communication unit,
    wherein the internal communication unit and the first controller are configured such that the first controller is started after the internal communication unit receives a first initiation code from the external communication unit.

2. The extracorporeal blood treatment apparatus of claim 1, further comprising a second controller for controlling performance of the treatment unit.

3. The extracorporeal blood treatment apparatus of claim 1, wherein the first initiation code comprises a first identification code and the internal communication unit comprises:
    a memory unit for storing a second identification code for identifying a patient; and
    a comparison unit for comparing the first identification code with the second identification code.

4. The extracorporeal blood treatment apparatus of claim 3, wherein the internal communication unit and the first controller are configured such that the preparation of the treatment unit begins when the first identification code matches the second identification code.

5. The extracorporeal blood treatment apparatus of claim 4, wherein the internal communication unit comprises a mobile telephone unit.

6. The extracorporeal blood treatment apparatus of claim 5, wherein the first initiation code comprises a short message in SMS format.

7. The extracorporeal blood treatment apparatus of claim 5, wherein the first initiation code comprises a voice message.

8. The extracorporeal blood treatment apparatus of claim 1, wherein the internal communication unit communicates via a communication network with the external communication unit.

9. A method for remotely activating the preparation of an extracorporeal blood treatment apparatus, wherein the extracorporeal blood treatment apparatus comprises:
    a treatment unit;
    a first controller for controlling the preparation of the treatment unit;
    an internal communication unit configured to communicate with an external communication unit, the method comprising the steps of:
    the first communication unit receiving a first initiation code from the external communication unit; and
    activating the first controller to begin preparation of the treatment unit for extracorporeal blood treatment.

10. The method for remotely activating the preparation of an extracorporeal blood treatment apparatus of claim 9, wherein the first initiation code comprises a first identification code and the internal communication unit comprises:
    a memory unit for storing a second identification code for identifying a patient; and
    a comparison unit for comparing the first identification code with the second identification code;
    the method further comprising the steps of:
    comparing the first identification code to the second identification code; and activating the first controller to begin preparation of the treatment unit for extracorporeal blood treatment when the first identification code matches the second identification code.

11. The method for remotely activating the preparation of an extracorporeal blood treatment apparatus of claim 10, wherein the external communication unit comprises a mobile telephone, the method further comprising:
the internal communication unit receiving the first identification code as a short message in SMS format from the external communication unit.

12. The method for remotely activating the preparation of an extracorporeal blood treatment apparatus of claim 10, wherein an external communication unit comprises a mobile telephone, the method further comprising:
the internal communication unit receiving the first identification code as a voice message from the external communication unit.

* * * * *

UNITED STATES PATENT AND TRADEMARK OFFICE
CERTIFICATE OF CORRECTION

PATENT NO. : 8,315,654 B2
APPLICATION NO. : 12/438775
DATED : November 20, 2012
INVENTOR(S) : Klaus Balschat et al.

Page 1 of 1

It is certified that error appears in the above-identified patent and that said Letters Patent is hereby corrected as shown below:

On the title page, please correct lines 6-7 of Item 57 (Abstract) as follows:

Please change "In order to the prepare the device blood treatment" to --In order to prepare the device for blood treatment--

Signed and Sealed this
Fourteenth Day of May, 2013

Teresa Stanek Rea
*Acting Director of the United States Patent and Trademark Office*